United States Patent [19]
Huber

[11] Patent Number: 5,825,495
[45] Date of Patent: Oct. 20, 1998

[54] BRIGHT FIELD ILLUMINATION SYSTEM

[75] Inventor: Edward D. Huber, Sunnyvale, Calif.

[73] Assignee: Lockheed Martin Corporation, Sunnyvale, Calif.

[*] Notice: The term of this patent shall not extend beyond the expiration date of Pat. No. 5,680,215.

[21] Appl. No.: 781,517

[22] Filed: Jan. 9, 1997

Related U.S. Application Data

[63] Continuation-in-part of Ser. No. 395,847, Feb. 27, 1995, Pat. No. 5,680,215.

[51] Int. Cl.$^6$ .................................................. G01B 11/30
[52] U.S. Cl. ........................ 356/371; 356/237; 345/131; 345/132
[58] Field of Search .................................. 356/371, 376, 356/237; 348/92, 128, 131, 132, 125

[56] References Cited

U.S. PATENT DOCUMENTS

| | | | |
|---|---|---|---|
| 4,488,172 | 12/1984 | Hutchin | 358/107 |
| 4,575,805 | 3/1986 | Moermann et al. | 364/474 |
| 4,641,972 | 2/1987 | Halioua et al. | 356/376 |
| 4,825,263 | 4/1989 | Desjardins et al. | 356/376 |
| 5,030,008 | 7/1991 | Scott et al. | 356/376 |
| 5,175,601 | 12/1992 | Fitts | 356/376 |
| 5,307,151 | 4/1994 | Hof et al. | 356/376 |
| 5,680,215 | 10/1997 | Huber et al. | 356/371 |

OTHER PUBLICATIONS

David R. Burton et al., "Multichannel Fourier fringe analysis an an aid to automatic phase unwrapping", *Applied Optics*, May 10, 1994, vol. 33, No. 14, pp. 2939–2948; U.S.A.

Chris L. Koliopoulos et al., "Real–Time Video Rate Phase Processor", *SPIE* vol. 2003 Interferometry VI, 1993, pp. 264–268; U.S.A.

Yiping Xu et al., "Simple and Effective Phase Unwrapping Technique", *SPIE* vol. 2003 Interferometry VI, 1993, pp. 254–263; U.S.A.

B.F. Oreb et al., "Moire Based Optical Surface Profiler for the Minting Industry", Preprint of article that appeared in *SPIE Proceedings*, vol. 1779, 1992, pp. 48–57; U.S.A.

Daniel Malacara, "Optical Shop Testing", John Wiley & Sons, Inc., 1992, pp. 668–681; U.S.A.

(List continued on next page.)

*Primary Examiner*—F. L. Evans
*Attorney, Agent, or Firm*—Fenwick & West LLP

[57] ABSTRACT

A Bright Field Illumination system for inspecting a range of characteristically different kinds of defects, depressions, and ridges in a selected material surface. The system has an illumination source placed near a first focus of an elliptical reflector. In addition, a camera facing the inspected area is placed near the illumination source and the first focus. The second focus of the elliptical reflector is located at a distance approximately twice the elliptical reflector's distance above the inspected surface. The elliptical reflector directs the light from the source onto the inspected surface. Due to the shape of the elliptical reflector, light that is specularly reflected from the inspected surface is directed into the camera is which located at the position of the reflected second focus of the ellipse. This system creates a brightly lighted background field against which damage sites appear as high contrast dark objects which can be easily detected by a person or an automated inspection system. In addition, the Bright Field Illumination system and method can be used in combination with a vision inspection system providing for multiplexed illumination and data handling of multiple kinds of surface characteristics including abrupt and gradual surface variations and differences between measured characteristics of different kinds and prior instruments.

20 Claims, 7 Drawing Sheets

OTHER PUBLICATIONS

Carolyn R. Mercer et al., "Fiber–Optic Projected–Finge Digital Interferometry", *NASA Technical Memorandum 103252—1990 Fall Conference on Halogram Interferometry and Speckle Metrology Sponsored by the Society for Experimental Mechanics, Baltimore, Maryland,* Nov. 4–7, 1990, pp. 1–8.

Katherine Creath., "WYKO Systems for Optical Metrology", *SPIE* vol. 816 Interferometric Metrology, 1987, pp. 111–126; U.S.A.

James C. Wyant, "Interferometric Optical Metrology; Basic Principles and New Systems", *Laser Focus,* May 1982, pp. 65–71; U.S.A.

FIG._2a

FIG_2b

FIG_3

FIG_4

FIG_5

(1) $\dfrac{X^2}{A^2} + \dfrac{Y^2}{B^2} = 1$ (2) $a + b = 2(c+d) = \text{constant}$

THEN:

(3) $A = c + d$ (4) $B = \sqrt{\left[\dfrac{(a\,b)}{2}\right]^2 - d^2} = \sqrt{c^2 + 2cd}$ (5) $D = E \cdot \left(1 - \dfrac{h}{d}\right)$

BRIGHT FIELD ILLUMINATION SYSTEM

CROSS-REFERENCE TO RELATED APPLICATIONS

This application is a continuation-in-part of U.S. patent application Ser. No. 08/395,847, filed on Feb. 27, 1995 by inventors Edward D. Huber and Rick A. Williams, entitled "VISION INSPECTION SYSTEM AND METHOD," now U.S. Pat. No. 5,680,215. This application is related to U.S. patent application Ser. No. 08/569,524, filed on Dec. 8, 1995 by inventors Edward D. Huber, Rick A. Williams, Dean M. Shough, Osuk Y, Kwon, and Rebecca L. Welling and entitled "CONTOUR MEASUREMENT SYSTEM," now U.S. Pat. No. 5,612,786, which is a continuation of U.S. patent application Ser. No. 08/249,841, filed May 26, 1994 and now abandoned.

STATEMENT OF GOVERNMENTAL INTEREST

This invention was made in part using funds provided under NASA contract NAS 10-10900. As such, the U.S. government has rights in this invention.

TECHNICAL FIELD

This invention relates generally to optical illumination systems and methods and more particularly to Bright Field Illuminators.

BACKGROUND OF THE INVENTION

Rapid inspection of large surfaces having different kinds of damage distributed irregularly to varying degrees of frequency is frequently problematic, particularly when it is desired to compare a current surface under inspection with a prior recorded surface data base. At present, damage inspections of particular kinds of material surfaces are on occasion done visually by a human inspector, operating perhaps with the aid of a magnifying glass and flashlight. This manual approach is, unfortunately, slow, labor intensive, and tedious. Further, manually generated inspection data is not readily accessible for review and analysis, because it is typically not already entered into a computer data base and requires further manual data entry and keyboarding subject to risk of human error. An example of the kinds of surfaces which may require rapid and reliable inspection, measurement, and comparison with prior inspection results are the thermal radiators or cargo-bay doors of a space shuttle. The radiators need to be inspected before and after every flight into space. The radiators are composite structures having a honeycombed core covered by an aluminum sheet overlaid by Permacel P-223 including Kapton and silicone adhesive and layers of Inconel, silver, and Teflon.

Currently the radiators are visually inspected, a task requiring up to three people working several shifts. Among different kinds of shuttle damage targeted for identification and characterization are microdamage features including punctures, scratches, and gouges over 0.005 inch in depth; and macrodamage features including dents over 0.008 inch in depth and over 0.25 inch in diameter, and delaminations over 0.008 inches in depth and over 0.25 square inch in area. It is desired that these damage features be localized within approximately plus or minus 0.1 inch. The particular kinds of surfaces inspected include thermal reflective tape, aluminum skin, and coolant flow lines.

Visual or video inspection systems, in general, and in particular those systems for automated large area inspection of small surface damage sites, require that the features of interest be readily distinguished from the object background other non-damaged areas. Current inspection systems and methods have several problems, including: 1) limited contrast between features of interest and the object background; 2) variability of background illumination due to the limited range of current illumination systems, thereby causing bright, or hot, spots instead of uniformly illuminated areas; and 3) variability of illumination coverage causing different feature highlighting of the inspected object, thereby resulting in varying interpretations of the same features.

Some Bright Field and Dark Field Illumination systems have been developed for use with microscope type inspection systems that produce high contrast images. These systems, however, are restricted to very small inspection areas. Further, the microscope type illumination systems share the microscope or imaging optics with the illuminating optics. For standard Bright Field Illumination Systems, the optics are usually used in a telecentric mode in which the illuminating light is collimated, or focused, at or near infinity, thus producing retro-reflection of the light off the inspected object. This mode adds the requirement that the optical components be as large as the object under inspection. This requirement presents a problem for using Bright Field Illumination of the conventional method for inspecting large areas.

SUMMARY OF THE INVENTION

The present invention is a method and system of providing background illumination highlighting small surface features for inspection and identification purposes. The present invention creates a brightly lighted background field against which damage sites or features appear as high contrast dark objects which can be easily detected by a person or an automated inspection system. The inventive method and system provides uniform, large area, Bright Field Illumination. In addition, the inventive method and system eliminates variability of feature highlighting during the inspection process.

The advantages of the Bright Field Illuminator system of the present invention are that it: 1) provides Bright Field Illumination without the restriction of sharing the illuminator and imaging optics because it does not require telecentric optics for the illumination, thereby allowing a very large bright field illumination using inexpensive, low quality optical components and allowing a large standoff distance from the object under inspection; and 2) takes the unique approach of focusing the illuminating light to a point approximately twice the distance from the illuminator source and camera to the inspected object surface. With the light focused in the inventive manner, the illuminator light is reflected from the surface under inspection directly into the viewing system without requiring retro-reflection.

Also according to the present invention, a vision inspection system (4) and method provides for multiplexed illumination and data handling of multiple kinds of surface characteristics including abrupt and gradual surface variations and differences between measured characteristics of different kinds and prior measurements. The present invention makes provisions to illuminate and identify both microfeatures as well as macrofeatures in selected material surfaces, permitting enhanced camera discrimination of the various kinds of features. According to the present invention, damage artifacts which are orders of magnitude smaller in lateral dimension extent than the others which may be much broader laterally without a comparable lateral contrast gradient, can be detected and measured. Such macrofeatures may be very gradual depth depressions or elevations, as when the damage is a delamination causing a formerly undeviated surface level to rise at a gradual rate with a lateral traversal. According to the present invention, assessment to a high degree of reliability of damage to embossed, specular, and highly reflective surfaces which have very few damage sites, i.e., typically from zero to five (but on occasion up to hundreds of damage sites) over a surface having hundreds of non-damaged features in a very large surface area covering more than 100 square meters, is possible.

More particularly, the present invention provides a vision inspection system (4) that can accurately measure the size and shape of cavities, ridges and depressions in material surfaces (7) of two basic kinds: micro damage, such as pin hole punctures, scratches, and cuts; and macro damage, such as shallow dents and tape material delaminations. The vision inspection system (4) according to the present invention automatically finds and identifies both large and small damage sites on selected material surfaces (7). The vision inspection system (4) according to the present invention is robotically mounted for automated scanning operation. Further, the vision inspection system (4) according to the present invention assesses, with high reliability, information with respect to damage to embossed, specular and highly reflective surfaces (7) having very few damage sites. Typically, zero to five, but on occasion hundreds would be present among hundreds of non-damaged features over a very large surface area covering more than 100 square meters. The inspection process is performed at a high rate to cover a large inspection surface area quickly.

The vision inspection system (4) according to the present invention further characterizes damage sites on a selected material surface (7) with first and second optical subsystems (20, 21). The first optical subsystem (20) highlights and finds small damage sites having cuts, scratches or micrometeor damage using a uniform broad source illuminator arranged to produce Bright Field Illumination ("BFI") that emphasizes abrupt damage sites to be detected by a video camera system. The second optical subsystem (21) is designed to highlight and measure larger, gradual damage areas such as dents and bubbles or delaminations of radiator tape on a space shuttle surface, for example. This optical subsystem (21) uses a white light projector to illuminate the radiator surface with fringe lines for surface contour measurement that is sensitive to surface deformations. The combination of these optical subsystems covers the expected range of damage with a high level of reliability. Video image data from optical subsystems is acquired and processed using a data processing system (14) conducting several stages of image processing and analysis enabling each damage site to be identified and fully characterized. The inspection data is stored in a new or revised database as a feature list for each damage site, and the large volume of video data processed is either discarded or archived.

During data acquisition in accordance with one embodiment of the present invention, first and second successive image frames are captured for the same illuminated region or patch of predetermined size, and inspection processing begins the interpretation of each of the two images separately. In particular, a micro-damage analysis according to the present invention processes BFI images where damage sites appear as high contrast dark spots or regions against a bright diffuse background and data is taken from microdamage locations to assess damage such as punctures or scratches, after a series of image processing and analysis steps to filter background clutter and characterize each damage site in terms of specific features such as location, size, and shape. The macro-damage detection procedure processes acquired fringe data to evaluate larger damage areas such as shallow dents or tape delaminations for generating a 3-D depth profile map which is filtered to remove background noise. Then, each damage site is characterized in terms of specific features. The accumulated damage or object data is stored in a data base available for follow-up testing, evaluation and reporting.

DETAILED DESCRIPTION OF THE PREFERRED EMBODIMENTS

Figure 1A:
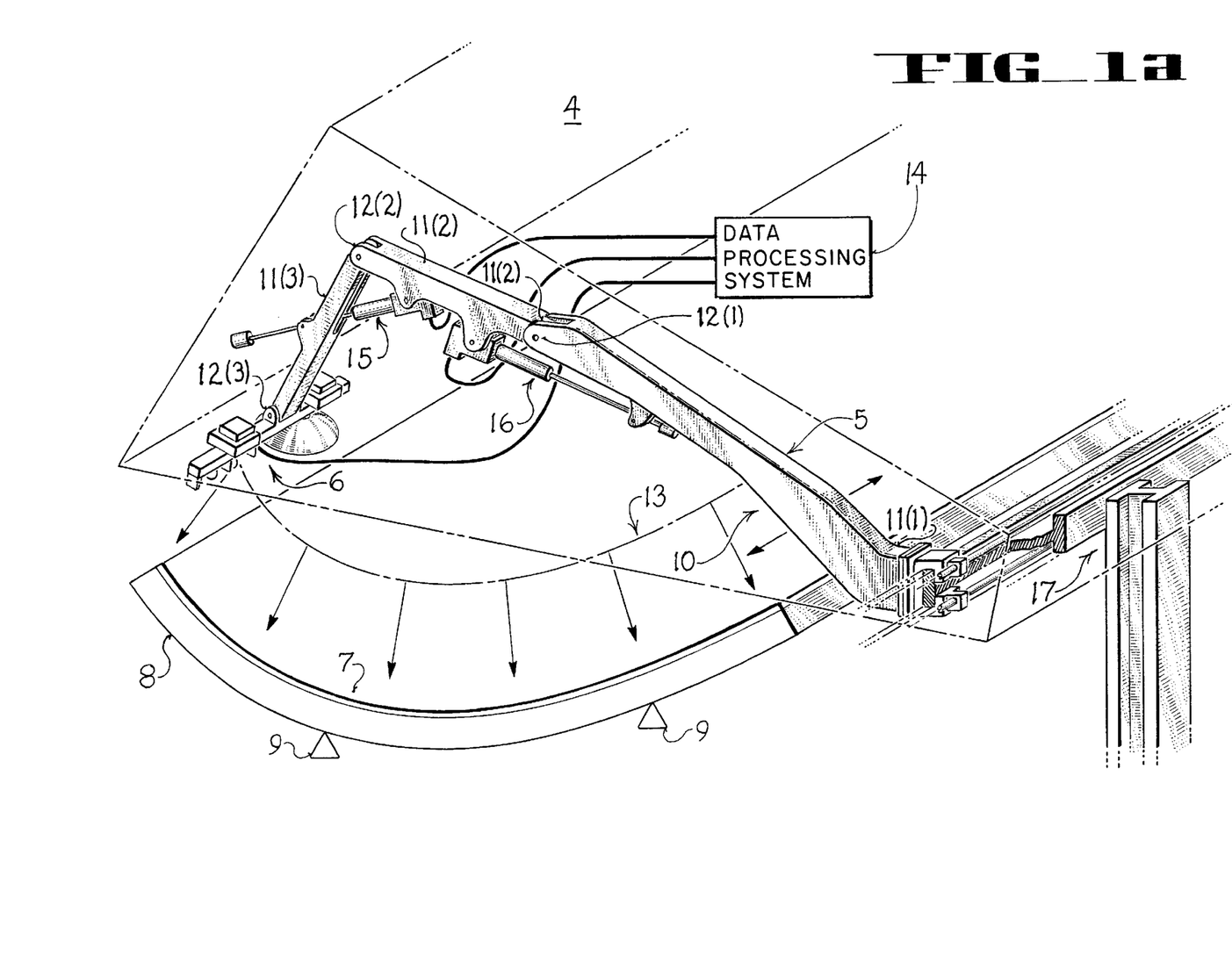
FIG. 1a is a side schematic diagram of the vision inspection system according to the present invention, including robotic and optical systems for multiplexed illumination and inspection of a material surface which may have defects of several characteristically different kinds.
Figure 1B:
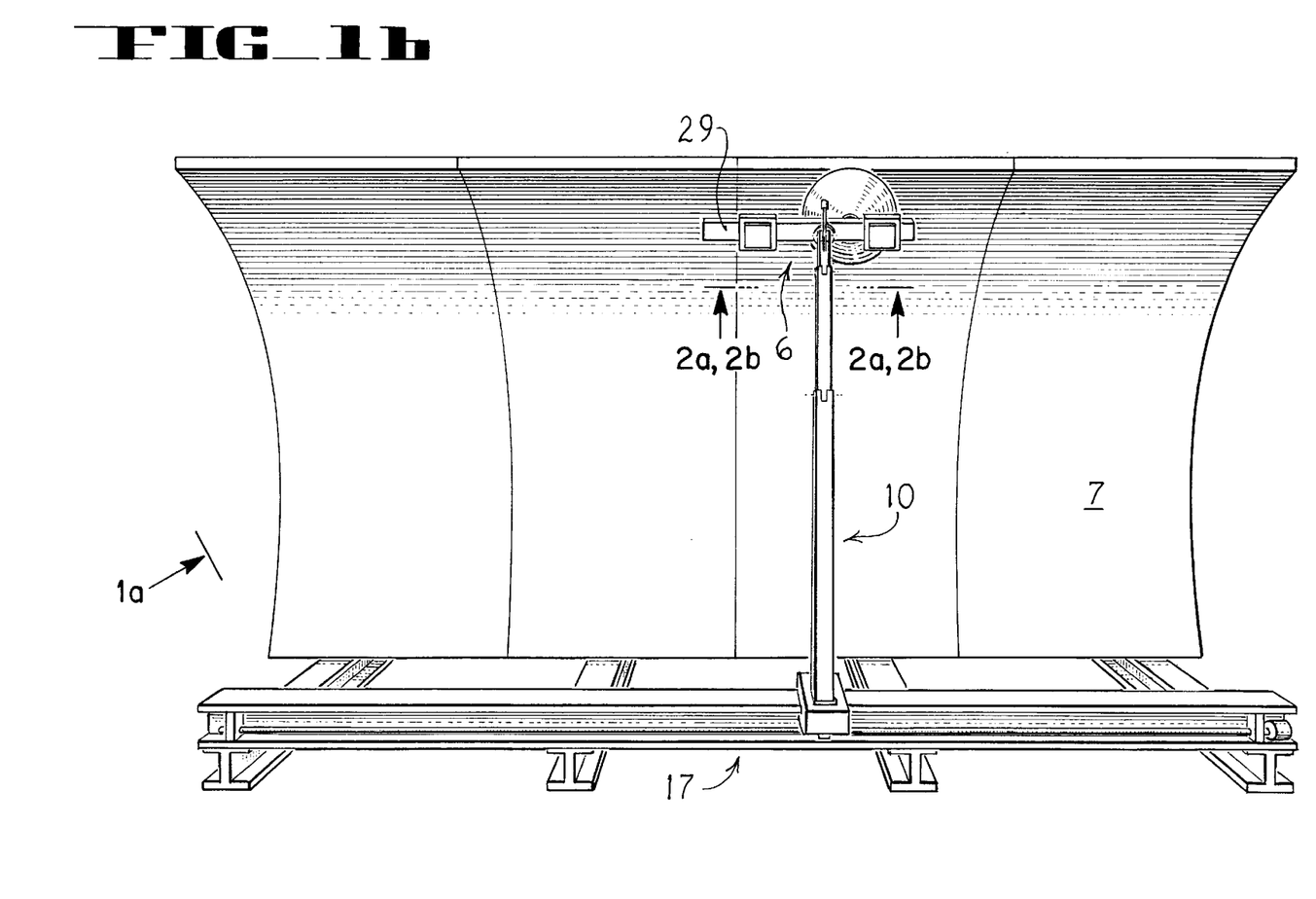
FIG. 1b is a top schematic diagram of the vision inspection system according to the present invention, including robotic and optical systems for multiplexed illumination and inspection of the same material surface.

FIG. 1a is a side schematic diagram of a vision inspection system 4 according to the present invention, including a portion of robot system 5, an optical system 6, and a data processing system 14 for multiplexed illumination and inspection of a selected material surface 7 which may have defects of several characteristically different kinds. In particular, material surface 7 of FIG. 1a may be metallic, ceramic, or comprised of selected composite materials. FIG. 1b is a top view of the elements shown in the side view in FIG. 1a. In the case of material surface 7 being a radiator door of a shuttle space vehicle, material surface 7 to be inspected may be a tape overlayer including laminations which are joined to a selected metallic undersurface 8. Undersurface 8 may in turn be held in place during inspection by selected supports 9. Robot system 5 according to the present invention includes an arm 10 including one or more limbs 11 respectively connected with joints 12, more particularly referred to as joints 12(1)–12(3). Limbs 11 include first through third limbs 11(1)–11(3). Limbs 11 are positionable relatively with respect to each other at joints 12 under control of data processing system 14 providing suitable electric control signals to drive C for example, hydraulic apparatus 15 and 16. Hydraulic apparatus 15 is connected to respective extensions of limbs 11(1) and 11(2), and hydraulic apparatus 16 is connected to respective extensions of limbs 11(2) and 11(3). Limb 11(1) is mounted on a laterally positionable frame 17 which adjusts arm 10 and optical system 6 axially along the contour of material surface 7 continuously or intermittently as arm 10 and optical system 6 inspect sections of material surface 7 along path 13. Thus, robot system 5 is used for positioning optical system 6 for vision inspection of selected material surface 7 along successive paths 13. Optical system 6 according to the present invention accomplishes multiplexed illumination and inspection of a material surface 7 which may have defects of several characteristically different kinds including microdamage, including, for example, abrupt defects including punctures and scratches; and macrodamage, including, for example, gradual defects including shallow dents or tape delaminations.

Figure 2A:
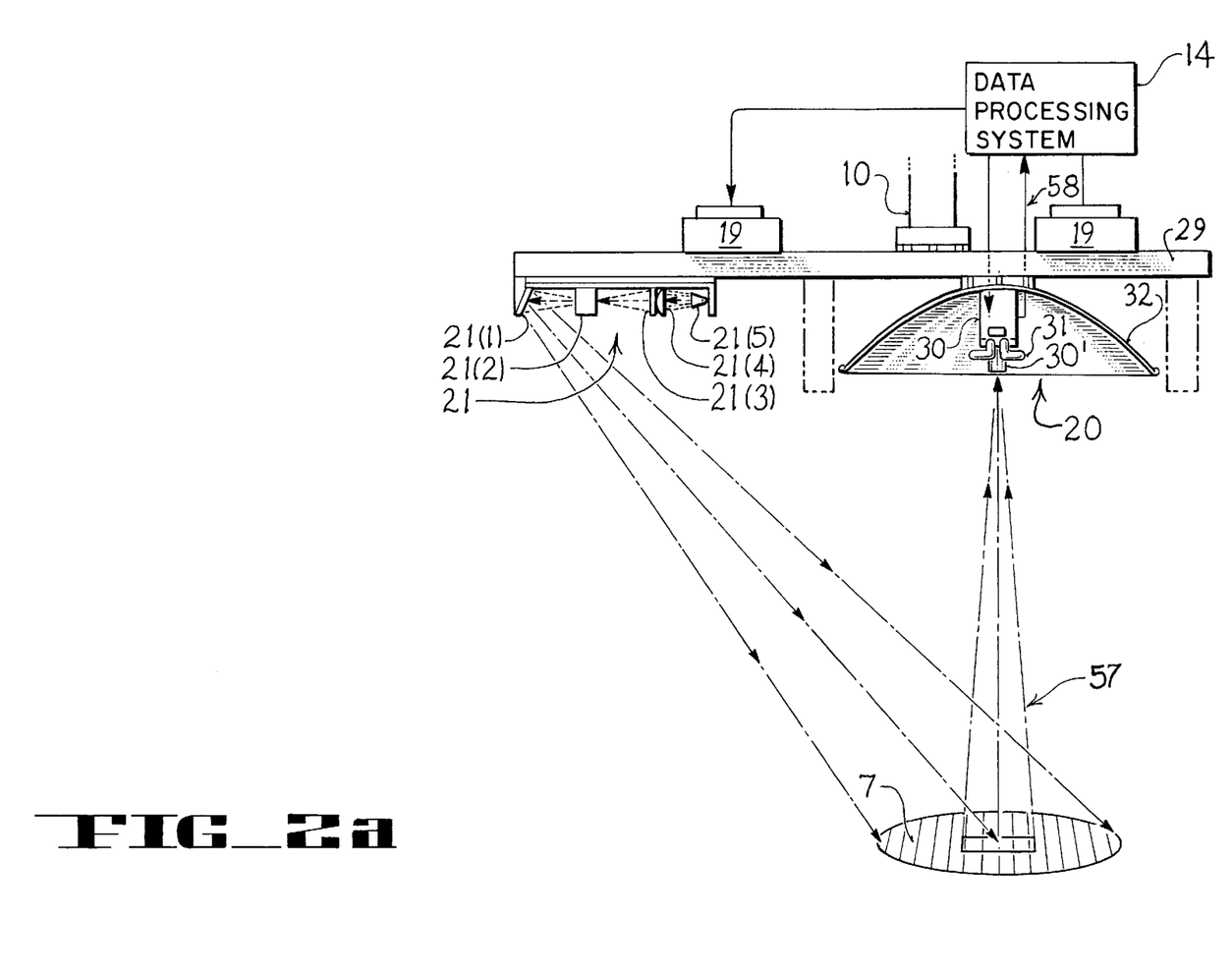
FIG. 2a shows a schematic diagram of the optical system according to the present invention, including two optical subsystems for multiplexed illumination of a material surface which may have defects of several characteristically different kinds, with indications of the operation of illumination by a second subsystem using fringe lines and the detection of the fringe lines by a video camera with respect to a predetermined patch of a selected material surface.
Figure 2B:
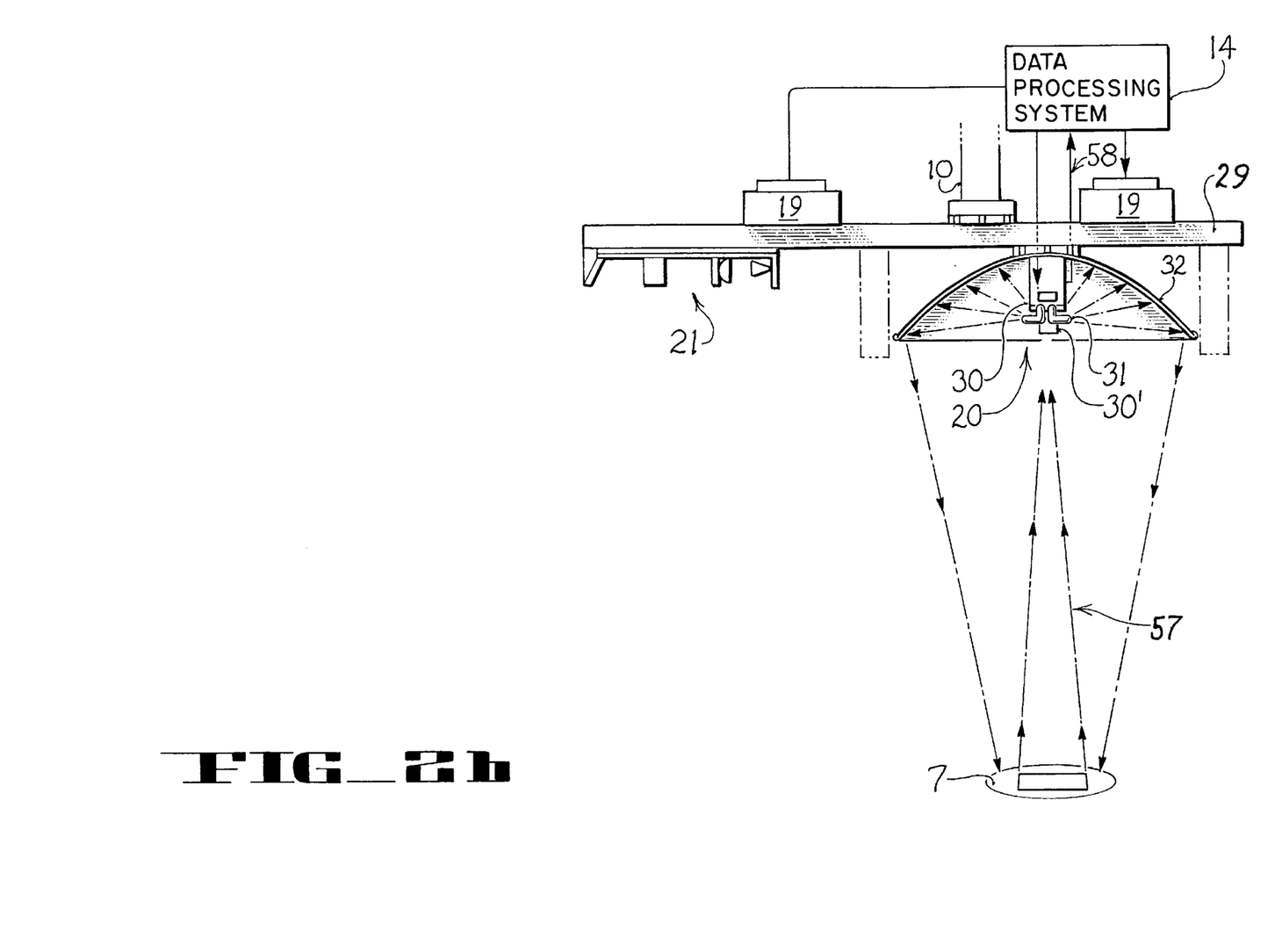
FIG. 2b shows a side schematic diagram of the optical system according to the present invention, including two optical subsystems for multiplexed illumination of a material surface which may have defects of several characteristically different kinds, with indications of the operation of bright field illumination by a first optical subsystem and the detection of the illuminated surface by a video camera with respect to a predetermined patch having abrupt contour defects or variations.

One embodiment of optical system 6 according to the present invention is shown in FIG. 2a including first and second optical subsystems 20 and 21 and a video camera 30. FIG. 2b shows these elements with an emphasis on the operation of BFI subsystem 20, while FIG. 2a emphasizes the operation of the fringe optical subsystem 21. Video camera 30 receives images from selected portions of surface 7 while illuminated by optical system 6. Video camera 30 is preferably electronic and desirably has sufficient resolution capabilities to detect imperfections, irregularities, and defects on or of material surface 7 which are targeted for detection. Electronic video camera 30 may look directly down or obliquely onto material surface 7 from a distance of about two feet above, for example. Visual scanning is accomplished by viewing approximate 5 inch by 5 inch patches during scanning in a continuous motion about 24 inches above the target surface under inspection, according to one embodiment of the present invention. Information is collected in predetermined data frames using strobed illuminators that "freeze" the motion of the scanner as data is taken every 4 inches along a predetermined sweep path. As an alternative to a video camera, other kinds of image detectors can be employed.

As indicated in FIGS. 1a and 1b, optical system 6 is mounted on arm 10 of robot system 5. An embodiment of the present invention including optical system 6 is shown in FIGS. 2a and 2b including a flash system 19, first and second optical subsystems 20 and 21, support structure 29, and a video camera 30, which are subject to control of data processing system 14 for directing the operation and positioning of robot system 5 as well as the timing of illumination bursts from first and second optical systems 20 and 21. Flash system 19 produces trigger signals which activate a selected one or both of first and second optical subsystems 20 and 21. First and second optical subsystems 20 and 21 accomplish multiplexed illumination of material surface 7. More particularly, robot system 10 controls the positioning of optical system 6 over selected portions and paths for viewing and illuminating material surface 7. Robot system 10 may, for example, conduct a raster illumination and detection scan of material surface 7. Optical subsystems 20 and 21 according to the present invention include respective first and second illumination systems, which are employed for illuminating material surface 7. Alignment of optical systems 20 and 21 ensures that first and second illumination systems 20 and 21 are positioned with respect to common portions of material surface 7 for visual inspection.

In lieu of separate optical subsystems 20 and 21, a single illumination system can be used, so long as the system is capable of producing time-separate illumination beams for multiplex operation, to provide suitable lighting to enable detection of different kinds of surface defects, irregularities, or damage. Optical subsystems 20 and 21 are multiplexed, by strobing for example, to provide illumination to predetermined patches along a specified path on material surface 7 by lighting first from one and then from the other of optical subsystems 20 and 21. Predetermined blank periods of non-illumination can be provided between pulses or strobes of one form of illumination and then the other. Further, more than two modes of illumination may be provided by use of additional separate illumination systems or optical subsystems, or by use of a single system which is constructed to produce selectably multiplexed lighting suitable for detection and measurement of different kinds of defects or surface variations including abrupt and gradual surface variations.

FIG. 2a particularly shows a side schematic diagram of optical system 6 according to the present invention, including first and second optical subsystems 20 and 21 and support structure 29 mounted at or near its center to joint 12(3). Optical system 6 accomplishes multiplexed illumination of material surface 7 with first and second optical subsystems 20 and 21. According to the preferred embodiment of the present invention indicated in FIGS. 2b and 2a, first and second optical subsystems 20 and 21 are both strobed illumination systems working with single video camera 30. First optical subsystem 20, according to an embodiment of the present invention, is a BFI system, which comprises a ring flash lamp 31 and an elliptical reflector 32. Ring flash lamp 31 is preferably mounted around video camera 30, and elliptical reflector 32 is located behind video camera 30 and ring flash lamp 31. Both ring flash lamp 31 and video camera 30 are located at or near one focus of elliptical reflector 32. The camera and imaging lens are located at the real image of the other focal point of elliptical reflector 32. This focal distance is located approximately twice the distance to material surface 7 from the one focus of elliptical reflector 32, so that the specular return light from material surface 7 uniformly fills the lens of video camera 30 over its entire viewing area. This method produces a BFI without the restriction of telecentric optics. This allows large area BFI with small camera imaging lenses of high optical quality and a large elliptical reflector 32 of low optical quality. This illumination produces a uniform, diffuse, bright background against which the small damage sites appear as high contrast dark spots or regions.

FIG. 2b shows a side schematic diagram of first optical subsystem 20 according to an embodiment of the present invention, for accomplishing large area BFI of a selected patch of material surface 7 which may have defects with abrupt contour variations. In particular, first optical subsystem 20 comprises ring flash lamp 31 mounted along a central axis of the concave surface of elliptical reflector 32. Axially oriented video camera 30 including viewing lens 30' is mounted along the axis of elliptical reflector 32 and within the annulus of ring flash lamp 31 in order to minimize surface illumination non-uniformity. Ring flash lamp 31 is preferably mounted around the viewing lens 30' of video camera 30, and elliptical reflector 32 is located behind video camera 30 and ring flash lamp 31. Both ring flash lamp 31 and video camera 30 are located at one focus of elliptical reflector 32. The distance between the elliptical surface and the first focal point is designed to provide minimal but adequate room for the camera 30 and lamp hardware 31. The other focal point of elliptical reflector 32 is located approximately twice the distance to material surface 7. Accordingly, elliptical reflector 32 directs the light from ring flash lamp 31 onto material surface 7. Elliptical reflector 32 is designed so that the light specularly reflected from the material surface 7 is directed into the viewing lens 30'. In addition, elliptical reflector 32 is preferably approximately twice the size of the area under inspection. Moreover, elliptical reflector 32 is preferably of low optical quality and its surface is buffed to a partially diffuse/specular finish in order to minimize illumination irregularities arising from secondary images that would appear from a highly polished reflector.

Figure 5:
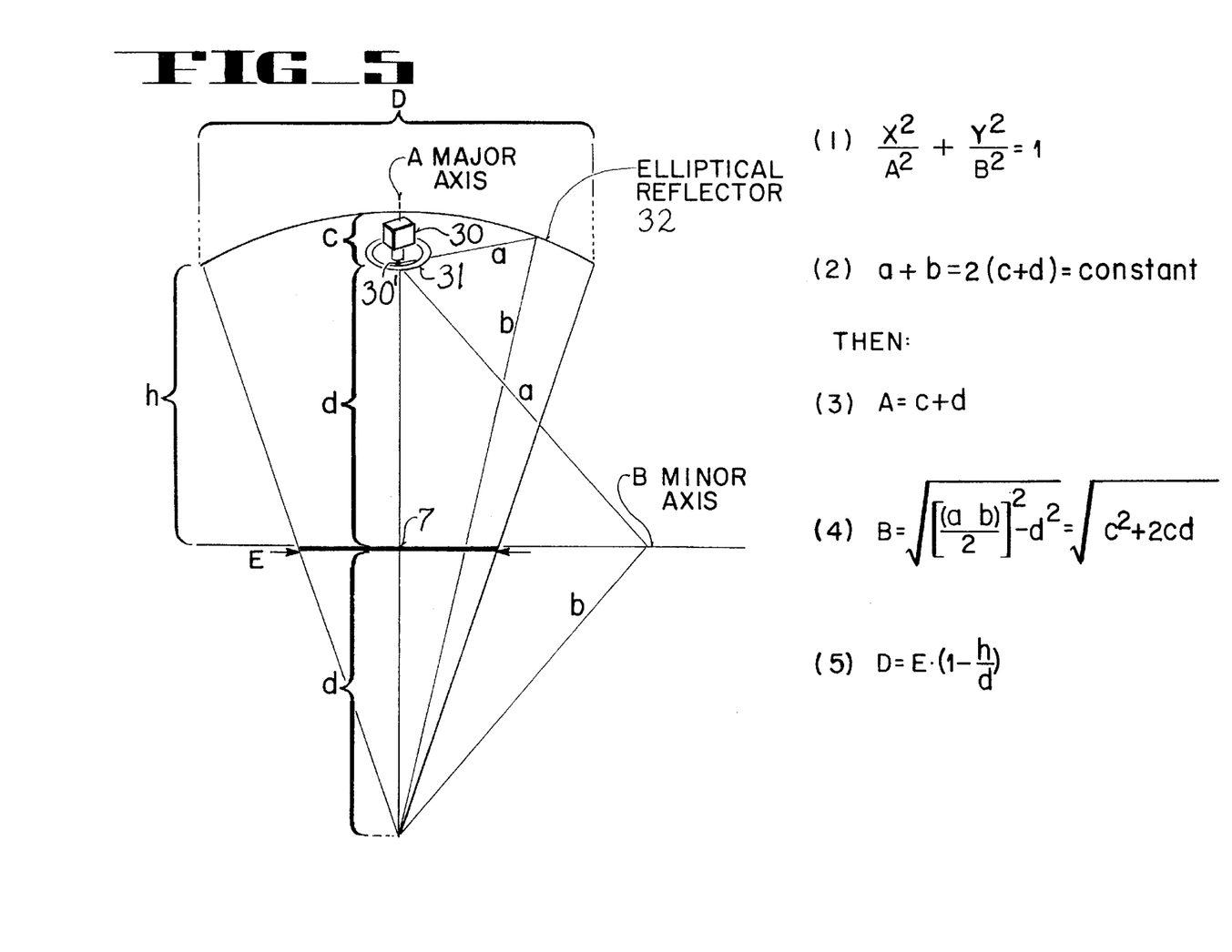
FIG. 5 illustrates a Bright Field Illuminator according to the present invention and the equations governing the illustrated optical configuration.

FIG. 5 illustrates a Bright Field Illuminator according to the present invention and the equations governing the illustrated optical configuration. Shown are elliptical reflector 32, camera 30, camera lens 30', ring flash lamp 31, and material surface 7. Also shown are the size of the illuminated area under inspection E, major axis A and minor axis B of elliptical reflector 32, distance C, which is the distance between elliptical reflector 32 and lens 30' measured along major axis A, distance h which is the height of the elliptical reflector 32 above the material surface 7 as measured along major axis A, diameter D, which is the diameter of elliptical reflector 32, distances a and b, which represent optical path lengths between the ellipse surface and its focii and distance d, which is the distance from the ellipse focii to its center. In the preferred embodiment, distance d approximately equals h. As is well known in the art, equations (1)–(5) explain how to design an elliptical reflector having desired optical characteristics. Note that in a preferred embodiment of the Bright Field Illuminator, C is 5 inches, d is 24 inches, and E is 9 inches. Accordingly, A is 29 inches, B is 16.28 inches, a+b is 58 inches, and D is 18 inches.

Figure 3:
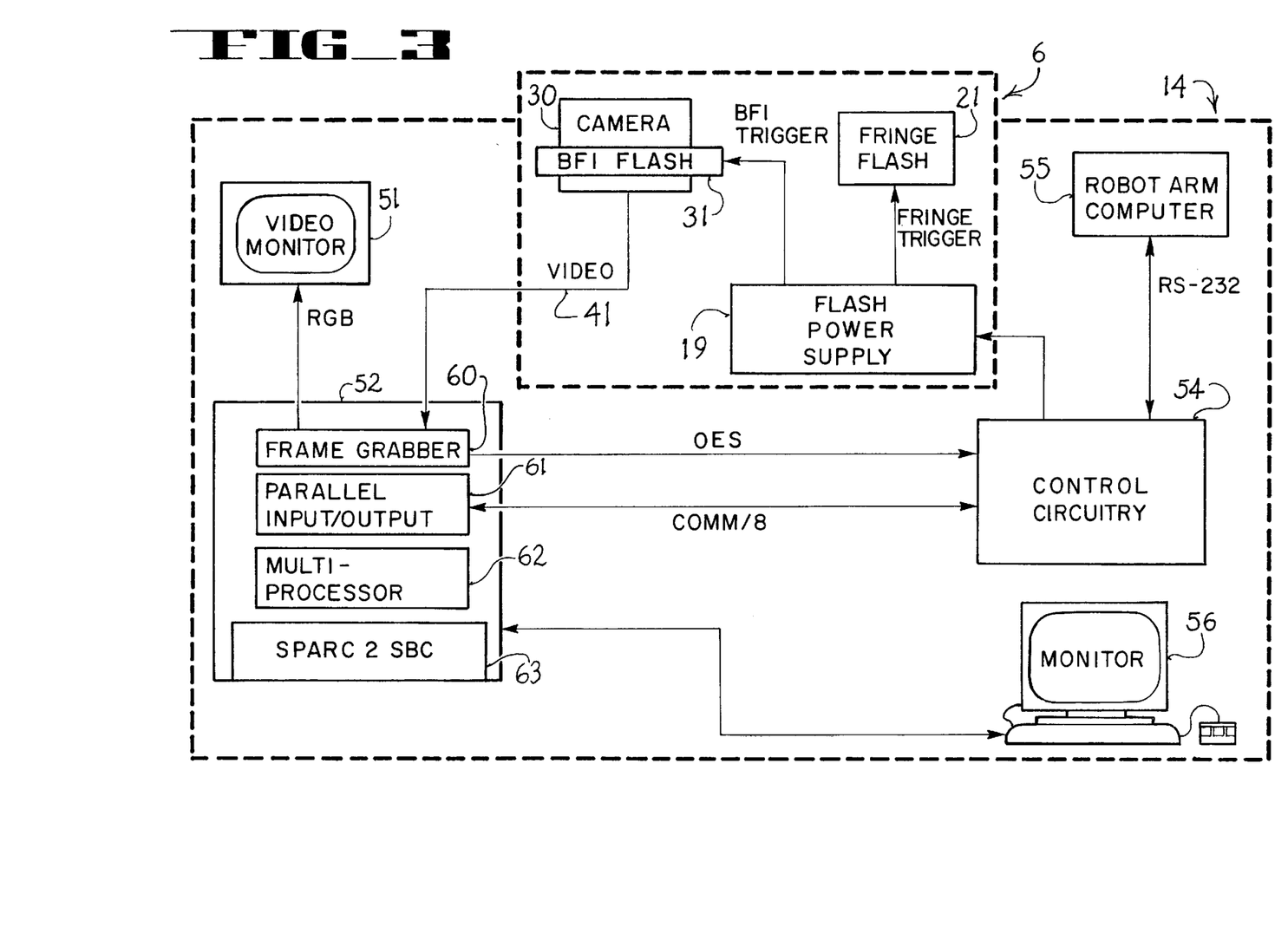
FIG. 3 shows a block diagram of the vision inspection system according to the present invention, including an embodiment of the present invention having an optical system and a data processing system.

Second optical subsystem 21 shown in FIGS. 2a and 2b is a slide projection type system (referred to as a fringe projector according to one embodiment of the present invention) which images a grating onto material surface 7. Details of the fringe projection approach are provided in related U.S. patent application Ser. No. 08/249,841 filed on May 26, 1994 by inventors Edward D. Huber, Rick A. Williams, Dean M. Shough, Osuk Y. Kwon, and Rebecca L. Welling, and entitled "CONTOUR MEASUREMENT SYSTEM." This patent application is assigned to the same assignee as herein and is incorporated herein by reference in its entirety. This patent application was abandoned in favor of FWC application Ser. No. 08/569,524 filed Dec. 8, 1995, now U.S. Pat. No. 5,612,786. Second optical subsystem 21 can be mounted onto a selected end of boom 29 as shown in FIGS. 2a and 2b. Second optical subsystem 21 according to one embodiment of the present invention is two feet in length, so that the angle between the fringe projector and video camera 30 is preferably about forty-five degrees. Video camera 30 receives image information from material surface 7 along image beam path 57 which is converted into a video signal provided along video line 58 to data processing system 14, which may be a general purpose computer or a processor of much simpler design and construction. The video information provided to data processing system 14 includes the results of illumination provided by both first and second optical subsystems 20 and 21. According to one embodiment of the present invention, the fringe projector of second optical subsystem 21 is any projector capable of illuminating material surface 7 with a set of fringe lines. The fringe projector may use a white light or a monochromatic light source. It may provide continuous, flash, or strobe illumination. The boresight of the light emanating from second optical system 21 may be perpendicular to material surface 7 or it may form an other than 90° angle therewith. The fringe lines falling on material surface 7 are made to have a sinusoidally varying intensity as seen by camera 30; this variation is in the x (horizontal) direction in the preferred embodiment. The fringe lines represent lines of maximum intensity. They are vertically disposed in this embodiment. These lines are 360° apart in phase. A selected fringe line establishes a reference for phase and position calculations during calibration and measurement operational modes. Camera 30 has a field of view encompassing all or part of a selected portion of material surface 7. Camera 30 may be any electronic camera, such as a CCD, CID, or Vidicon camera or film. The boresight of camera 30 may be perpendicular to material surface 7, or may form an other than 90° angle therewith. The image plane of camera 30 is divided into a set of pixels, e.g., 640 horizontal×480 vertical pixels. Camera 30 may or may not employ frame integration. The image data recorded by camera 30 are fed into data processing system 14. Control circuitry 54 in FIG. 3 is coupled between computer 52 and optical system 6. The purpose of control circuitry 54 is to synchronize camera 30 with optical system 6 and its optical subsystems 20 and 21, in part when optical subsystem 21 is flashing or strobing, within a projector to produce fringe lines patterns on material surface 7 in a spatial phase shifting embodiment. Fringe lines projected onto material surface 7 that are not completely straight and exhibit bumps in the horizontal dimension indicate the presence of a contour on material surface 7, i.e., a change in its depth (z) dimension. According to one embodiment of the present invention, a three-bucket algorithm with three frames, or a four-bucket algorithm is used, wherein the frames are, relatively speaking, at 0° phase, 90° phase, 180° phase, and 270° phase for reasons indicated below. The four-bucket algorithm is less prone to errors than the three-bucket algorithm, but takes more processing time. Another alternative method is the Carré method. In the Carré method, the phase shifts between frames can be other than 90°. These are just three examples of algorithms borrowed from phase-shifting interferometry. Any phase-shifting algorithm may be used in the present invention. Following the calculation of the phase map and the unwrapping of the phases, the computed phases are then converted into calculated three-dimensional coordinates by applying the system calibration parameters to each pixel data point, using the system geometry equations and the results of a calibration procedure discussed below. The finalized image data can then be represented as a fully-dimensioned three-dimensional object that can be measured or viewed on the display of computer monitor 56 in any orientation, using conventional software.

With respect to FIG. 2a, a preferred embodiment of second optical subsystem 21 comprises a lamp 21(5) that produces a light beam which illuminates through a heat filter 21(3) and illuminator optics 21(2) onto a grating pattern (not shown) which has been formed, e.g., on a transparent slide that is held in place by slide holder. The illuminated grating pattern is then projected by projection lens onto material surface 7. The requisite phase shifting of the sinusoidal grating pattern is achieved by a method, known as spatial phase shifting, in which the slide holder is not physically moved, and camera 30 takes just one exposure. The data phase shifting is accomplished by means of data processing system 14 processing neighboring pixels that are approximately at 90°, and 180° (and, for four-bucket algorithms, 270°) in phase apart from the original set of pixels corresponding to the first frame at 0°. Other phase-shifting techniques are possible. A test calibration fixture can be used to provide a set of points in three-dimensional space whose coordinates are known very accurately relative to one another. The location of a particular point determined by measuring three adjacent surfaces and then computing their unique intersection point. Each calibration fixture comprises a variety of multi-faceted shapes that are rigidly mounted to a structure to insure their geometrical stability. A test calibration fixture is characterized by a plurality of substantially identical truncated pyramids each having countersunk pins. The calibration procedure for the present invention is described in the cross-referenced patent application.

FIG. 3 shows a block diagram of vision inspection system 4 according to a first embodiment of the present invention, including optical system 6 and data processing system 14 of vision inspection system 4. Data processing system 14, according to one embodiment, includes a video monitor 51, a VME computer system 52, control circuitry 54, robot arm computer 55, and computer monitor 56 connected to VME computer system 52. Other computer systems can be substituted for VME computer system 52. According to one embodiment of the present invention, VME computer system 52 includes a VME chassis with an embedded Sun Microsystems SPARC 2 single board computer (SBC) 63. Connected to the chassis of VME computer system 52 is a frame grabber 60 such as for example a FG100-VME frame grabber unit manufactured by Imaging Technology, Inc., of Massachusetts, a digital parallel input/output unit 61, a multiprocessor 62, and an embedded SPARC 2 processor 63. Multiprocessor 62 may include one or more cards of multiple processors each connected into the VME chassis and including one or more processors which operate as slaves to embedded SPARC 2 SBC, in order to speed image processing operation. Frame grabber 60 receives analog video information from video camera 30 with respect to viewed surface regions 7. The analog signal information is converted into digital form in frame grabber 60 which then provides the received view in digital form to video monitor 51 for operator observation of single frames of information. Control circuitry 54 is connected to frame grabber 60 along an OES signal line, which represents odd even synchronization information regarding whether odd or even video lines are being processed by frame grabber 60. Additionally, an eight-bit COMM/8 line connects control circuitry 54 with parallel input output card 61, enabling the transmission of command control and synchronization information to ensure that information is received by frame grabber 60 at the appropriate illumination times by triggering first and second optical subsystems 20 and 21. Further, control circuitry 54 is connected along a two-way RS232 line with robot arm computer 55. Additionally, monitor 56 is connected to frame grabber 60. As suggested above, optical system 6 includes flash system 19, camera 30, and first and second optical subsystems, 20 and 21, respectively a BFI flash system and a fringe flash system. Respective first and second optical subsystems 20 and 21 receive trigger signals from flash system 19 which includes a camera flash unit and a flash power supply. Separate trigger signals are provided to first and second optical subsystems 20 and 21, with the BFI flash receiving a BFI flash trigger signal and the fringe flash receiving a fringe trigger signal. According to an embodiment of the present invention, first and second optical subsystems 20 and 21 are alternately triggered, so that a particular selected surface region is alternately illuminated and consequently the frames observed by camera 30 represent multiplexed inspection patterns produced under different lighting conditions, in one case adapted to optimize detection and measurement of abrupt surface changes and in the other case adapted to optimize detection and measurement of gradual surface changes.

Figure 4:
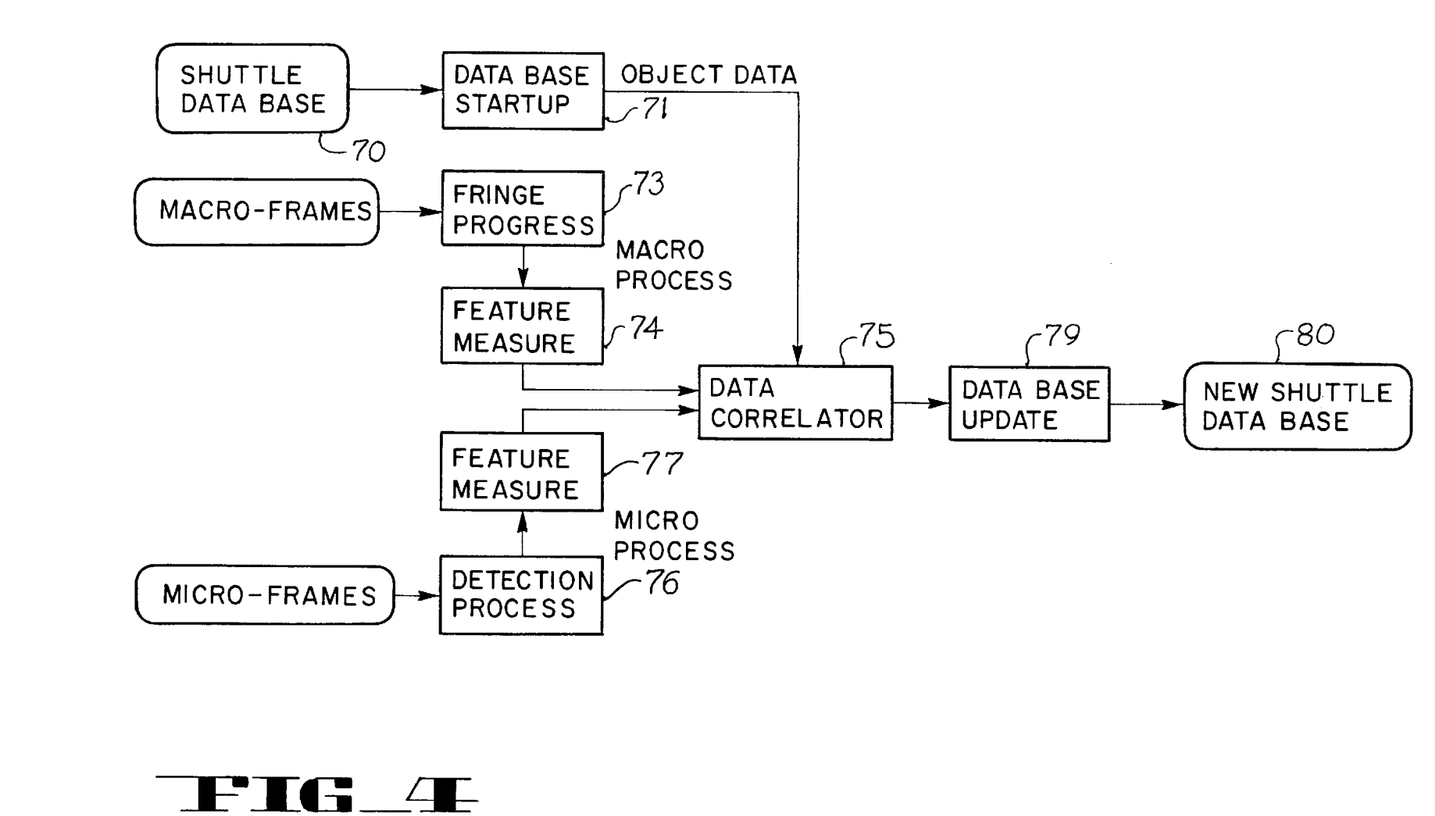
FIG. 4 is a flow chart of operation of a vision inspection system according to the present invention.

FIG. 4 is a flow chart of operation of a vision inspection system 4 according to the present invention. According to an embodiment of the present invention, a reference shuttle data base 70 which has previously been constructed is started up 71 to produce object data. Alternatively, operation can begin with a null data base which does not contain any object data. However, if object data has already been collected, according to one embodiment of the present invention, the data base includes measured objects which are characterized according to a predetermined set of object features, such as closed rectangles or ovals, or open figures such as lines or curves, to name several examples. For each feature of an object, predetermined information regarding to parameters specific to the particular feature of an object are included in the data base to specifically identify the qualities of the particular object. The reference shuttle data base 70 stores all radiator measured objects including both artifact and damage information, and this data base is used to initialize the radiator inspection process with known artifact and damage information. The reference shuttle data base 70 includes object data including location data, and feature data, without limitation. The reference shuttle data base 70 further includes an active features list. Reference shuttle data base 70 further includes a features list, as well as, according to one embodiment, the actual radiator image data stored in toto on optical data or video data disk storage. The object data is provided to a data correlator 75 to enable removal of known artifacts and damage from a current data assembly of new objects, permitting retention in the final data base only of new and unknown 'damage-like' objects. Data correlator 75 further correlates object data from both micro and macro data processes, to prevent retention of multiple object representations of the same physical structure. In summary, data correlator 75 accomplishes data correlation in first and second steps, by first accomplishing positional data correlation of macrodata and microdata, and then by accomplishing positional and feature correlation of the results of macro and micro data correlation to eliminate features which amount to no variation from an earlier shuttle database.

Macroframe data which is read by camera 30 is fringe processed 73 and subject to feature measurement 74 and then provided to a data correlator 75 for subsequent data correlation. According to one embodiment of the present invention, the detected image frame information is averaged or shrinked to increase the signal to noise ratio of the information acquired. Next, raw phase information is calculated, based upon a surface profile modulo 1 fringe spacing, according to one embodiment of the present invention. For example, according to one embodiment of the present invention, a four-bucket algorithm is used, wherein the frames are, relatively speaking, at 0° phase, 90° phase, 180° phase, and 270° phase for reasons indicated below. Another alternative method is the Carré method. In the Carré method, the phase shifts between frames can be other than 90°. These are just two examples of algorithms borrowed from phase-shifting interferometry. Any phase-shifting algorithm may be used in the present invention. The raw phase information is then unwrapped to generate a full surface profile amounting to a 3-D profile map of a selected patch of material surface 7 based upon macroframe features. In particular, following the calculation of a phase map and the unwrapping of the phases, the computed phases are then converted into calculated three-dimensional coordinates by applying the system calibration parameters to each pixel data point, using the system geometry equations and the results of a calibration procedure detailed in the cross-referenced patent application. The finalized image data can then be represented as a fully-dimensioned three-dimensional object that can be measured or viewed on the display computer monitor 56 in any orientation, using conventional software. A detection filter is applied to the surface profile data. Then, the detected objects are labeled. Similarly, microframe data is read by camera 30 and is detection processed 76.

Next, the microframe data is subject to feature measurement 77. Feature measurement 77 provides measurement data of selected non-damage features to avoid filling the data base with expected features. Measurement of multiple features on an object enable separation of new damage from previously measured artifacts or damage. Accordingly, several features are measured on each detected "damage-like" object, and selection of good feature sets is accomplished by a selected feature performance analysis. Generic aspects of features include length, width, size, rotation angle, shape and the like. Artifact features include bolt-likeness, tape edge-likeness and the like. Next, finalized image data is developed with the use of selected image segmentation techniques. The finalized image data are then used to detect and label potential damage sites.

The data developed according to the system and process of FIG. 4, in respective feature measurement functions 74 and 77 for microdamage and macrodamage frames is then provided to a data correlator 75 for data correlation based upon preestablished object data produced during data base start-up. The purpose of data correlation is to correlate object data from the separate micro and macro damage processes and to correlate object data with known artifacts and damage from a previous data base. Further, a purpose of data correlation is to remove known artifacts and damage from the new object list to pass only new and unknown "damage-like" objects. Both positional and feature correlation is accomplished, to accommodate changes in artifacts and changes in damage. The results of correlation 75 are provided 79 to make a data base update, resulting in a new shuttle data base 80.

The present invention has been particularly described above in terms of certain exemplary embodiments. However, practitioners skilled in the art of optical design, after having perused the foregoing description and the accompanying drawing, could readily develop design forms for other embodiments without departing from the scope of the present invention. Therefore, the present invention is defined more generally by the following claims and their equivalents.

What is claimed is:

1. A large area bright field illuminator for illuminating an inspected area, the illuminator comprising:

an elliptical reflector having first and second focii;

a lamp located in the vicinity of the first focus; and a camera located at a reflected image of the second focus and in the vicinity of the first focus, the camera having a lens; wherein the inspected area is situated approximately midway between the first and second foci, so that specularly reflected return light from the inspected area uniformly fills a viewing area of the lens.

2. The illuminator of claim 1, wherein the lamp is a ring flash lamp mounted around the camera.

3. The illuminator of claim 1, wherein a sectional diameter of the elliptical reflector is approximately twice a diameter of the inspected area.

4. The illuminator of claim 1, wherein a reflective surface of the elliptical reflector has a partially diffuse finish.

5. A bright field illumination system for inspecting an area, the system comprising:

a camera having a lens facing the inspected area;

a light source capable of emitting light; and a reflector for reflecting non-collimated emitted light towards the inspected area so that light incident on the inspected area is specularly reflected into the lens to produce uniform intensity bright field illumination across the inspected area.

6. The system of claim 5, wherein the light source strobes the emitted light.

7. The system of claim 5, wherein the light source is a ring lamp.

8. The system of claim 7, wherein the ring lamp is situated around the camera.

9. The system of claim 5, wherein the reflector is an elliptical reflector focusing the light specularly reflected from the inspected area into the camera lens.

10. The system of claim 9, wherein the elliptical reflector has a sectional diameter approximately twice a diameter of the inspected area.

11. The system of claim 5, wherein a reflective surface of the reflector has a partially diffuse finish.

12. The bright field illumination system of claim 5, wherein a size of the inspected area is not limited by a size of the camera lens.

13. An optical system for inspecting characteristically different kinds of variations in a surface, the system comprising:

first and second optical subsystems for multiplexed illumination of a predetermined sequence of selected common portions of a material surface region under optical inspection sequenced in alternating succession;

the first optical subsystem providing bright field illumination;

the second optical subsystem providing fringe illumination taking into account phase information;

an inspection subsystem for viewing common portions of material surface regions in connection with illumination by the first and second optical subsystems; and a data processing system for processing optical inspection data from both the first and the second optical subsystems; wherein the second optical subsystem comprises a module for performing ordered phase unwrapping, in which a raw phase map having many pixels is produced, and a quality metric is applied to each pixel in the raw phase map to rank pixels for an order in which the pixels will be unwrapped.

14. The optical system of claim 13, wherein the first optical subsystem comprises:

a camera having a lens facing the surface;

a light source capable of emitting light;

a reflector reflecting the emitted light towards the surface so that the light incident on the surface is specularly reflected into the lens.

15. The optical system of claim 14, wherein the light source strobes the emitted light.

16. The optical system of claim 14, wherein the light source is a ring lamp.

17. The optical system of claim 16, wherein the ring lamp is situated around the camera.

18. The optical system of claim 14, wherein the reflector is an elliptical reflector focusing the light to a point approximately twice the distance from the camera to the surface.

19. The system of claim 18, wherein the elliptical reflector has a sectional diameter approximately twice a diameter of the inspected area.

20. The system of claim 14, wherein a reflective surface of the reflector has a partially diffuse finish.

* * * * *